United States Patent [19]

Laguzza et al.

[11] Patent Number: 4,801,688

[45] Date of Patent: Jan. 31, 1989

[54] HYDRAZONE IMMUNOGLOBULIN CONJUGATES

[75] Inventors: Bennett C. Laguzza; Cynthia L. Nichols, both of Indianapolis, Ind.

[73] Assignee: Eli Lilly and Company, Indianapolis, Ind.

[21] Appl. No.: 106,756

[22] Filed: Oct. 7, 1987

Related U.S. Application Data

[63] Continuation of Ser. No. 867,183, May 27, 1986, abandoned.

[51] Int. Cl.$^4$ ............... A61K 39/44; C07K 3/08; C07K 15/14
[52] U.S. Cl. ................... 530/391; 424/85.91
[58] Field of Search ............... 530/391; 424/85

[56] References Cited

U.S. PATENT DOCUMENTS

| | | | |
|---|---|---|---|
| 3,387,001 | 6/1968 | Hargrove | 260/287 |
| 3,392,173 | 7/1968 | Hargrove | 260/286 |
| 4,166,810 | 9/1979 | Cullinan | 260/244.4 |
| 4,203,898 | 5/1980 | Cullinan | 260/244.4 |
| 4,522,750 | 6/1985 | Ades et al. | 530/397 |
| 4,596,676 | 6/1986 | Cullinan III | 530/816 X |
| 4,671,958 | 6/1987 | Rodwell et al. | 424/85 |

FOREIGN PATENT DOCUMENTS

| | | |
|---|---|---|
| 88695 | 9/1983 | European Pat. Off. . |
| 124502 | 11/1984 | European Pat. Off. . |
| 175617 | 3/1986 | European Pat. Off. . |
| 173629 | 3/1986 | European Pat. Off. . |
| 1446536 | 8/1976 | United Kingdom . |
| 1523980 | 9/1978 | United Kingdom . |
| 2090837 | 1/1982 | United Kingdom . |
| 2137202 | 10/1984 | United Kingdom . |
| 2137210 | 10/1984 | United Kingdom . |

OTHER PUBLICATIONS

Willan et al., FEBS Letters, 80 133 (1977).
Timofeev et al., FEBS Letters, 89 191 (1978).
Murayama et al., Immunochemistry, 15 523 (1978).
O'Shannessy et al., Immunology Letters, 8 273 (1984).
Chua et al., Biochimica and Biophysica Acta, 800 291 (1984).
Rothfus et al., J. Biol. Chem., 238 1402 (1963).
Blair et al., J. Immun. Meth., 59 129 (1983).
Ghose et al., Methods in Enzymology, 93 280 (1983).
Neuss et al., Tetrahedron Letters, 783 (1968).
Barnett et al., J. Med. Chem., 21, 88 (1978).
Conrad et al., J. Med. Chem., 22 391 (1979).
Root et al., FACSS 3nd National Meeting, Oct. 6-10, 1975, Abstract 183.
Langone et al., Anal. Biochem., 95 214 (1979).
Teale et al., Brit. J. Clin. Pharm., 4 169 (1977).
Johnson et al., Brit. J. Can., 44 372 (1981).
Rowland et al., Cancer Immunology and Immunotherapy, 19 1 (1985).
Bumol et al., Proc. Am. Assn. Cancer Research, 25 356 Abstract 1410 (1984) (Bumol I).
Bumol et al., Federation Proceedings, 44 1864 Abstract 8484 (1985) (Bumol II).
Bumol et al., J. Cellular Biochemistry, Supplement 9A Abstract 0124 (1985) (Bumol III).

*Primary Examiner*—Howard E. Schain
*Attorney, Agent, or Firm*—Robert A. Conrad; Leroy Whitaker

[57] ABSTRACT

Immunoglobulin conjugates formed by reaction of an antineoplastic indole-dihydroindole vinca alkaloid containing a hydrazine group attached at C-3 or C-4 with an oxidized glycoprotein containing aldehyde groups.

20 Claims, No Drawings

HYDRAZONE IMMUNOGLOBULIN CONJUGATES

This application is a continuation, of application Ser. No. 867,183, filed 5/27/86, now abandoned.

BACKGROUND OF THE INVENTION

Immunoglobulins are glycoproteins, i.e., oligosaccharides are attached to the protein at various sites. Vicinal diols of these oligosaccharides can be oxidized with periodate to yield dialdehydes, and the aldehyde groups thus produced reacted with various amines and hydrazines to form Schiff bases and hydrazones. For example, Willan et al., *FEBS Letters*, 80 133 (1977) oxidized an oligosaccharide attached to an asparagine residue at position 297 (using the numbering system of the human IgG1 myeloma protein Eu) in the $C_H2$ region of rabbit IgG. This oxidized material was, after purification, reacted with 4-amino-2,2,6,6-tetramethylpiperidine-1-oxyl free radical and the resulting imine (reaction of amino group with sugar aldehyde) reduced with $NaBH_3CN$ to yield a spin labelled protein. Timofeev et al., *FEBS Letters*, 89 191 (1978) also used oxidized glycoprotein monoclonal antibodies to prepare spinlabeled material. Murayama et al., *Immunochemistry*, 15 523 (1978) labeled periodate oxidized oligosaccharide-groups in an immunoglobulin (IgG) with amino-containing compounds via Schiff base formation. Aspartic acid and horseradish peroxidase were the "amines" employed. The aspartic acid-Schiff base was used to detect the antigenicity of human IgG by counter immunoelectrophoresis. et al., *Immunology Letters*, 8 273 (1984), coupled biotin hydrazide with aldehyde groups of oxidized immunoglobulins and suggested the use of the procedure for conjugation of fluorescent dyes to monoclonal antibodies.

Chua et al., *Biochimica and Biophysica Acta*, 800 291 (1984), oxidized carbohydrate groups on the constant region of the heavy chain of IgM (which has a relatively high carbohydrate content) to yield aldehydes. These aldehyde groups were reacted with hydrazide groups linked to a liposomal membrane. The monoclonal IgM antibodies were specific to a protein carrying a 1-dimethylamino naphthalene-5-sulfonyl haptan.

Rothfus et al., *J.B.C.*, 238 1402 (1963) used periodate oxidation followed by borohydride reduction to determine the identity of the sugar component of the glycopeptide from human gamma globulin.

The linking of cytotoxic agents to immunoglobulins is reviewed by Blair et al., *J. Immun. Meth.*, 59 129 (1983) and by Ghose, Blair and Kulkarni, *Methods in Enzymology*, 93 280 (1983). Blair et al. reveal, at page 130, the possibility of linking the cytotoxic agent to the oligosaccharide of an Ig. Oxidation to an aldehyde and coupling of the cytotoxic agent to the aldehyde is not mentioned. Ghose et al. cover much of the same ground, but do mention specifically the periodate oxidation of rabbit anti-BSA IgG having attached oligosaccharides to form aldehyde groups and the reaction of these groups with ethylenediamine followed by borohydride reduction of the Schiff base double bond to form new aminoethyl primary amine groups attached to the oligosaccharide portion of the glycoproteins.

EPO Application publication 88695 broadly claims processes described in the above publications; reaction of an aldehyde derived by oxidation of a carbohydrate moiety with a hydrazine, hydrazide or amine linker group of a compound to form a conjugate. The application is apparently directed to linker groups which are conjugated to the aldehyde-antibody and the linker group itself attached to an insoluble support or a second compound. There are also claims to antibody conjugates comprising any compound attached to a carbohydrate moiety of an antibody via a covalent hydrazone, imine or enamine bond. More specific claims are to a peptide linker, an amino acid linker or a linker of the general formula $W(CH_2)_nQ$ where W is $C_6H_5NH-CH_2-$ or $-CH_2-$ and Q is an amino acid, peptide, chelator or chelator derivative. Drugs specifically disclosed for antibodymediated delivery via this system are listed in Table 1 and includes these antineoplastic agents, daunomycin, bleomycin, vinblastine, vincristine, and 5-fluorouracil. There is no teaching of how these drugs are to be linked and, specifically, no teaching of how VLB or vincristine are to be linked since neither contains a hydrazide or amine function. Coupling to Fab antibody fragments is emphasized. Specific disclosure is limited to coupling ALKERAN® (N-[Bis($\beta$-chloroethyl)phenyl]alanine) and monoclonal antibodies against sheep red blood cells. No in vivo data are provided.

VLB, vincristine, and other antineoplastic drugs have been linked to immunoglobulins or other proteins.

U.K. patent application G.B. No. 2,090,837A discloses immunoglobulin conjugates covalently linked to a vinca moiety by amide formation. The amide bond itself is produced by the reaction of a vinca indole-dihydroindole alkaloid such as 4-desacetyl-VLB via a C-3 carboxazide group with a free amino group of an immunoglobulin or immunoglobulin fragment. The azide is prepared from 4-desacetyl-VLB-3-carboxhydrazide which is itself prepared by the action of hydrazine on VLB. The covalent bond formed between the vinca moiety and the immunoglobulin is not ordinarily reversible; i.e., the bond is not subject to hydrolytic (chemical) cleavage at physiological pH.

U.S. Pat. No. 4,203,898 (Cullinan I) discloses and claims 3-carboxazides of vinca indole-dihydroindole alkaloids such as VLB, vincristine, etc. It is these azides which were used in preparing the covalently linked immunoglobulin conjugates of the previous reference. The azide is prepared from a 4-desacetyl-3-carboxhydrazide of an indole-dihydroindole alkaloid. Such hydrazides are also disclosed and claimed.

U.S. Pat. No. 4,166,810 (Cullinan II) discloses a group of derivatives of 4-desacetyl-VLB-3-carboxhydrazide including $N^2$-alkyl derivatives. The compounds are prepared by forming a hydrazone upon reaction of the $N^2$ amine group with an aldehyde or ketone and then reducing the resulting enamine.

Neuss et al., *Tetrahedron Letters*, 783 (1968), disclose leurosine hydrazide.

Barnett et al., *J. Med. Chem.*, 21 88 (1978), also disclose the hydrazides of VLB and related indoledihydroindole derivatives.

Conrad et al., ibid, 22 391 (1979), discuss generally the amides of VLB and their activities as anti-cancer drugs. The same amides discussed above in connection with Cullinan I are disclosed herein. In addition, a bridged disulfide, compound 30, was prepared in which the carboxamide group was attached to an ethyldithioethylcarboxamide grouping. The corresponding primary amine containing the disulfide bond is compound 38. Also disclosed are radioimmune assays for VLB and vincristine. The radioimmune assay was developed by coupling 4-desacetyl-vinblastinoic acid azide (4-desacetyl-VLB-3-carboxazide) to BSA. This antigen was used to prepare antibodies in rabbits which antibody would then pick up the VLB moiety of the antigen. The amount of antigen was determined by using VLB labeled with tritium—see also Root et al., F.A.C.S.S., 2nd National Meeting, Oct. 6-10, 1975, Abstract 183.

Hargrove, U.S. Pat. Nos. 3,392,173 and 3,387,001, discloses novel C-4 esters of VLB, vincristine, leurosidine, etc. Among these esters is a chloroacetyl ester, which derivative was employed in EPO No. 124,502 to couple with a protein. Hargrove II reacted this 4-chloroacetyl ester with amines to prepare, for example, an N,N-dimethylglycine ester—vinglycinate.

Langone et al., Anal. Biochem., 95 214 (1979), developed radioimmune assays for vinblastine and vincristine. The antigens used were prepared by oxidizing VLB to a dicarboxylic acid and then coupling this product to a protein with a carbodiimide coupling reagent.

Teale et al., Brit. J. Clin. Pharm., 4 169 (1977), also developed radioimmune assays for vinblastine and vincristine. The vinca alkaloid is conjugated to the albumin by a Mannich reaction using an amine group in the protein (BSA), formaldehyde and vinblastine. The point of attachment of the vinca alkaloid, vinblastine or vincristine, is not specified.

Johnson et al., Brit. J. Can., 44 372 (1981), disclose the preparation of vindesine linked to anti-CEA immunoglobulin via an azide. [It should again be emphasized that the azide from desacetyl VLB and the azide congener of vindesine are identical since the compounds differ only as to the moiety on the C-3 carboxylic acid and this moiety (ester or amide) disappears after the coupling reaction.] These conjugates were found to be cytotoxic for human cancer cells in vitro. U.K. patent application GB No. 2,090,837, inventors Rowland and Simmonds, covers the same subject matter.

Rowland et al., Cancer Immunology and Immunotherapy, 19 1 (1985), discuss the anti-tumor properties of vindesine-monoclonal antibody conjugates (4-desacetylVLB derivatives conjugated via the C-3 carboxazide group as in U.K. patent No. 2,090,837A and Johnson et al). Four conjugates were tested against human tumor xenografts in athymic mice, and all showed some anti-tumor activity. Vindesine was inactive at non-toxic levels with the same tumor.

EPO No. 124502 covers conjugates prepared from an immunoglobulin and a 4-desacetyl-VLB or vindesine or other 4-desacetyl-VLB-3-carboxamide linked via a 4-succinate; i.e., a bridging group or linker between the 4-hydroxy group and the protein. The bridging group of the structure can be CO-CH$_2$ (from a 4-chloroacetyl group) or CO(CH$_2$)$_n$—CO (succinic or glutaric acid). The same 4-succinoyl derivatives are disclosed in United Kingdom patent application GB No. 2,137,202, and conjugates formed therefrom are disclosed in GB No. 2,137,210.

Bumol et al., Proc. Am. Assn. Cancer Research, 25 356 Abstract 1410 (1984) (Bumol I), discuss the characteristics of a conjugate prepared according to GB patent No. 2,137,210; i.e., a 4-desacetyl-4-succinoyl-VLB conjugate with a monoclonal antibody to a human adenocarcinoma (KS1/4). Bumol et al., Federation Proceedings, 44 1864 Abstract 8484 (1985) (Bumol II) discuss a similar conjugate with a monoclonal antibody to a human melanoma. Bumol et al., J. Cellular Biochemistry, Supplement 9A Abstract 0124 (1985) (Bumol III), discuss further work on the 4-desacetyl-4-succinoyl-VLB KS1/4 conjugate (adenocarcinoma).

None of the above references disclose or suggest conjugating an amine or hydrazine derivative of an antineoplastic dimeric indole-dihydroindole alkaloid with an oxidized carbohydrate (oxidized to one or more aldehyde groups) on the surface of a monoclonal antibody which is also a glycoprotein.

SUMMARY OF THE INVENTION

This invention provides conjugates formed by reaction of an oxidized glycoprotein containing one or more aldehyde groups with a vinca hydrazide. The hydrazide group can be either a C-3 carboxhydrazide (COR in formula I below) or a C-4 hydrazide-containing ester linked (R$^6$ in formula I below) via a hydrocarbon chain.

The vinca portion of the conjugate is described by Formula I below. The conjugates of this invention are formed by reaction of a compound of structure I with the aldehyde groups of an oxidized glycoprotein.

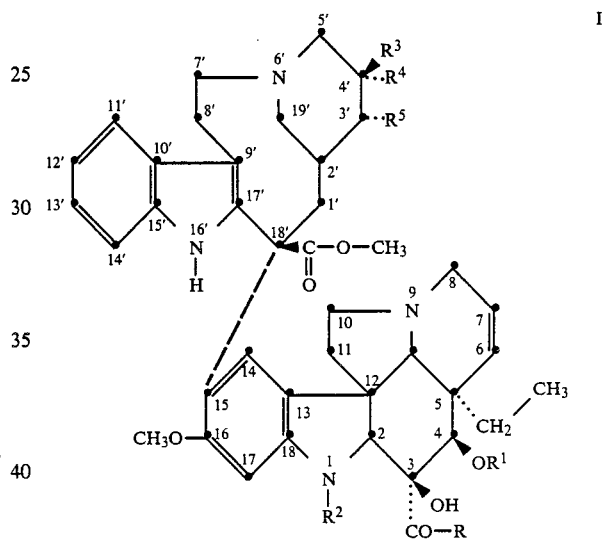

wherein R$^2$ is H, CH$_3$ or CHO; when R$^4$ and R$^5$ are taken singly, R$^5$ is H, and one of R$^3$ and R$^4$ is ethyl and the other is H or OH; when R$^4$ and R$^5$ are taken together with the carbons to which they are attached, they form an oxirane ring in which case R$^3$ is ethyl; R is NHNH$_2$,

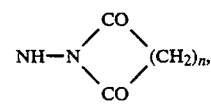

O(C$_{1-3}$ alkyl), NH$_2$, NH(C$_{1-3}$ alkyl), NH-CH$_2$CH$_2$-Y, 1-pyrrolidinyl or 1-piperidinyl, wherein n is 2-4 and Y is Cl, OCH$_3$ or SCH$_3$; R$_1$ is H, (C$_{1-3}$ alkyl)-CO, chloro-substituted (C$_{1-3}$ alkyl)-CO or R$^6$ wherein R$^6$ is COX-CONHNH$_2$ wherein X is C$_{1-4}$ straight chain alkylene, C$_{2-8}$ branched chain alkylene, C$_{2-4}$ alkenylene, C$_{3-4}$ alkynylene, C$_{3-6}$ cycloalkylene, phenylene, hydroxysubstituted C$_{1-4}$ alkylene, or a direct bond, except that R cannot be NHNH$_2$ when R$^1$ is R$^6$ and R$^1$ cannot be R$^6$ when R is NHNH$_2$. Groups illustrative of X in the above formulas include methylene, ethylene, propylene, butylene, vinyl, propylene, butenylene, butynylene, propynylene, hydroxyethylene, 1,2-dihydroxyethylene, 1,2-dimethylethylene, 1,2,3,4-tetrahydroxybutylene, 3,4-dimethylbutylene, 1,4-cyclohexylene, 1,4-phenylene, 1,2-phenylene, and the like.

Indole-dihydroindole alkaloids useful in preparing the hydrazides which form the conjugates of this invention, can be represented by the following 2-dimensional structure

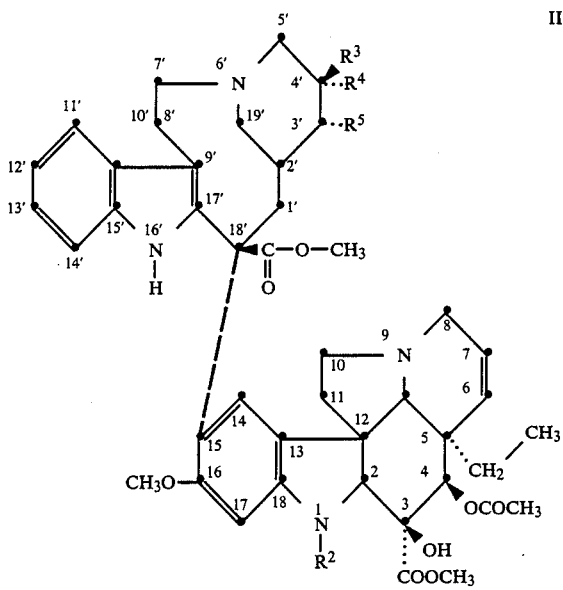

wherein $R^2$, $R^3$, $R^4$, and $R^5$ have their previous meaning.

In formula II above, where $R^2$ is methyl, $R^3$ is hydroxyl, $R^4$ is ethyl and $R^5$ is H, VLB (vinblastine) is represented; where $R^2$ is formyl, $R^3$ is hydroxyl, $R^4$ is ethyl and $R^5$ is H, vincristine (VCR) is represented; where $R^2$ is methyl, $R^3$ is ethyl, $R^4$ is hydroxyl, and $R^5$ is H, leurosidine is represented; where $R^2$ is methyl or formyl, $R^3$ is ethyl and $R^4$ and $R^5$ taken together with the carbons to which they are attached form an alpha-epoxide ring, leurosine and leuroformine, respectively, are represented; where $R^2$ is methyl, $R^3$ is ethyl, and $R^4$ and $R^5$ are H, deoxy VLB "B" (4'-deoxyleurosidine or 4'-epideoxy VLB) is represented; where $R^2$ is methyl, $R^4$ is ethyl and $R^3$ and $R^5$ are H, deoxy VLB "A" or 4'-deoxy VLB is represented; and where $R^2$ is CHO, $R^3$ is ethyl, $R^4$ and $R^5$ are H, 4'-epideoxyvincristine (1-formyl1-desmethyl-4'-deoxyleurosidine) is represented.

Literature references to the parent vinca alkaloids (II) are as follows: leurosine (U.S. Pat. No. 3,370,057), VLB (U.S. Pat. No. 3,097,137), leurosidine (vinrosidine) and leurocristine (to be referred to hereafter as vincristine) (both U.S. Pat. No. 3,205,220), desmethyl VLB (U.S. Pat. No. 3,354,163), 4'-epivincristine (U.S. Pat. No. 4,143,041), leuroformine, formylleurosine (U.S. Pat. No. 4,279,816), and deoxy VLB "A" and "B" [*Tetrahedron Letters*, 783 (1958)].

The hydrazides useful in forming the conjugates of this invention are prepared differently, depending on whether the hydrazide is attached at C-3 or C-4. The C-3 hydrazides are prepared by the procedure of U.S. Pat. No. 4,203,898, col 12, line 65 et seq. and Example 3, col 18. In this procedure, anhydrous hydrazine is reacted with a vinca alkaloid according to formula II in ethanol in a sealed tube at about 60° C. The product of this reaction is a 4-desacetyl 3-carboxhydrazide since the acetoxy group at C-4 is hydrolysed under the basic reaction conditions. If it is desirable to prepare an ester at C-4 ($R^1$ in I is ($C_{1-3}$ alkyl)-CO or chloro ($C_{1-3}$-alkyl)-CO), the C-3 carboxhydrazide according to I wherein $R^1$ is H is first protected by reaction with acetone to form an $N^2$-propylidene derivative. With the acylable $NH_2$ group of the hydrazide effectively protected against acylation, this "protected" derivative can then be acylated in routine fashion with an acyl halide (chloroacetyl chloride for example) or an acyl anhydride (propionic anhydride for example). The protecting group can then be removed by treatment with acid. If acylation also occurs on the C-3 hydroxyl, as it usually does, this C-3 acyl group can be preferentially removed by treatment with wet silica gel—see Hargrove, U.S. Pat. No. 3,392,173.

When the hydrazide group is part of a C-4 chain (i.e., part of $R^6$ in I above), the 4-desacetyl starting materials are prepared as follows, depending on the nature of the C-3 group: where C-3 is an ester group, the 4-desacetyl derivative is prepared by the procedure of Hargrove, U.S. Pat. No. 3,392,173, Examples 1-5; where C-3 is an amide group, the 4-desacetyl is prepared by the procedure of Conrad et al., supra, or Cullinan, U.S. Pat. No. 4,203,898. This procedure involves preparation of a C-3 carboxhydrazide which is accompanied by hydrolysis at C-4. The hydrazide is then converted to the azide and the azide reacted with ammonia or a primary amine of the structure $NH_2$-($C_{1-3}$ alkyl), or with $NH_2$—CH$_2$—CH$_2$—S—CH$_3$, $NH_2$—CH$_2$—CH$_2$—O—CH$_3$, pyrrolidine, piperidine or $NH_2$—CH$_2$—CH$_2$—Cl. A preferable method of preparing this last compound, the chloroethylamide to yield the desired C-3 carboxamide C-4 hydroxyl derivative is by decomposition of a 3''-($\beta$-chloroethyl)-3-spiro-5''-oxazolidine-2'',4''-dione of a vinca alkaloid according to formula II above. The preparation of these oxazolidinedione derivatives is set forth in Miller and Gutowski, U.S. Pat. No. RE 30,560. The preparation of the $\beta$-chloroethylamide from the above oxazolidinedione is set forth in Example 1 of Miller and Gutowski U.S. Pat. No. 4,357,334. (Example 2 of the same patent prepares the same $\beta$-chloroethylamide using the classical azide process). The primary amide (R in formula I is $NH_2$) can also be prepare by direct ammonolysis or by reduction of the hydrazide with Raney Nickel—see also U.S. Pat. No. 4,203,898. Finally, when R in I is

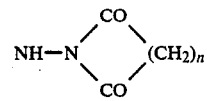

where n is 2-4; i.e., a cyclic succinimide, glutarimide, or adipimide, respectively, the 4-hydroxyl derivatives are prepared by the procedure set forth in the copending application of Cullinan, Ser. No. 745,562, filed 6-17-85.

The following list illustrates some of the vinca derivatives of Formula I which may be employed in this invention and their common names as known in the art:

4-Desacetyl-VLB-3-carboxhydrazide (Formula I, R=NHNH$_2$; $R^1$=$R^5$=hydrogen; $R^2$=methyl; $R^3$=hydroxy; $R^4$=ethyl)

4-Desacetyl-VLB-4-hemisuccinate hydrazide (R=OCH$_3$; $R^1$=COCH$_2$CH$_2$CONHNH$_2$; $R^2$=methyl; $R^3$=hydroxy; $R^4$=ethyl; $R^5$=hydrogen)

4-Desacetyl-VLB-3-carboxhydrazide-$N^2$-succinimide-4-hemisuccinate hydrazide

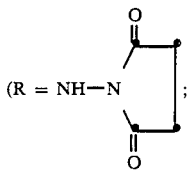

$R^1$=COCH$_2$CH$_2$CONHNH$_2$; $R^2$=methyl; $R^3$=hydroxy; $R^4$=ethyl; $R^5$=hydrogen)

4-Desacetyl-VLB-3-carboxamide-4-hemisuccinate hydrazide (R=NH$_2$; $R^1$=COCH$_2$CH$_1$CONHNH$_2$; $R^2$=methyl; $R^3$=hydroxy; $R^4$=ethyl; $R^5$=hydrogen)

4-Desacetyl-VLB-4-hemiglutarate hydrazide (R=OCH$_3$; $R^1$=COCH$_2$CH$_2$CH$_2$CONHNH$_2$; $R^2$=methyl; $R^3$=hydroxy; $R^4$=ethyl; $R^5$=hydrogen)

4-Desacetyl-VCR-4-hemisuccinate hydrazide R=OCH$_3$; $R^1$=COCH$_2$CH$_2$CONHNH$_2$; $R^2$=CHO; $R^3$=hydroxy; $R^4$=ethyl: $R^5$=hydrogen)

4-Desacetyl-4'-epideoxy-VLB-4-hemisuccinate hydrazide (R=OCH$_3$; $R^1$=COCH$_2$CH$_2$CONHNH$_2$; $R^2$=methyl; $R^3$=ethyl; $R^4$=$R^5$=hydrogen)

4-Desacetyl-VLB-3-carboxhydrazide-N$^2$-glutarimide-4-hemisuccinate hydrazide

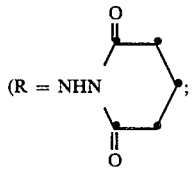

$R^1$= COCH$_2$CH$_2$CONHNH$_2$; $R^2$=methyl; $R^3$=hydroxy; $R^4$=ethyl; $R^5$=hydrogen)

4-Desacetyl-VCR-3-carboxhydrazide (R=NHNH$_2$; $R^1$=$R^5$=hydrogen; $R^2$=CHO; $R^3$=hydroxy; $R^4$=ethyl)

4-Desacetyl-4'-epideoxy-VLB-3-carboxhydrazide (R=NHNH$_2$; $R^1$=$R^4$=$R^5$=hydrogen; $R^2$=methyl; $R^3$=ethyl)

4-Desacetyl-VLB-3-ethylcarboxamide-4-hemisuccinate hydrazide (R=NHCH$_2$CH$_3$; $R^1$=COCH$_2$CH$_2$CONHNH$_2$; $R^2$=methyl; $R^3$=hydroxy; $R^4$=ethyl; $R^5$=hydrogen)

4-Desacetyl-VLB-3-methoxyethylcarboxamide-4-hemisuccinate hydrazide (R=NHCH$_2$CH$_2$OCH$_3$; $R^1$=COCH$_2$CH$_2$CONHNH$_2$; $R^2$=methyl; $R^3$=hydroxy; $R^4$=ethyl; $R^5$=hydrogen)

4-Desacetyl-VLB-4-propionyl-3-carboxhydrazide (R=NHNH$_2$; $R^1$=COCH$_2$CH$_3$; $R^2$=methyl; $R^3$=hydroxy; $R^4$=ethyl; $R^5$=hydrogen).

The preparation of several cyclic amides and their salts from application Ser. No. 745,562 follows:

Preparation I

4'-Deoxy-4-desacetylleurosidine-3-carboxhydrazide-N$^2$-succinimide

A solution was prepared from 1320 mg of 4'-deoxy-4-desacetylleurosidine-3-carboxhydrazide in 25 ml of pyridine. 175 mg of succinic anhydride were added and the reaction stirred at room temperature under nitrogen for about 24 hours. The volatile constituents were then removed from the reaction mixture in vacuo and the resulting residue taken up in methylene dichloride plus sufficient methanol to solubilize the entire residue. The organic layer was twice washed with an equal volume of water and was then dried. Evaporation of the volatile constituents in vacuo gave a residue comprising N$^2$-succinoyl 4'-deoxy-4-desacetylleurosidine3-carboxhydrazide which residue was dissolved in 25 ml of pyridine to which 350 mg of acetic anhydride were added, thus forming a mixed anhydride of the succinic and acetic acids, which anhydride spontaneously cyclized to yield 4'-deoxy-4-desacetylleurosidine-3-carboxhydrazide-N$^2$-succinimide. The reaction mixture was evaporated to dryness in vacuo and the residue was dissolved in methylene dichloride. The methylene dichloride extract was washed twice with an equal volume of water and then dried. Evaporation of the methylene dichloride yielded 4'-deoxy-4-desacetylleurosidine-3-carboxhydrazide-N$^2$-succinimide which was chromatographed over silica gel using ethyl acetate containing increasing amounts (0–50%) of methanol as the eluant. Fractions shown by TLC to contain the desired succinimide derivative were combined and the solid evaporated therefrom in vacuo. 190 mg of 4'-deoxy-4-desacetylleurosidine-3-carboxhydrazide-N$^2$-succinimide were obtained having the following physical characteristics:

Infrared spectrum (in chloroform): peaks at 3470, 1736, 1615, and 1572 cm$^{-1}$.

NMR (CDCl$_3$): δ at 10.90, 7.88, 7.49, 7.12, 6.48, 6.05, 5.80, 4.10, 3.76, 3.56, 2.82, 0.93, 0.85.

The sulfate salt was prepared by dissolving the free base in anhydrous ethanol at pH=~8.0. The pH was then adjusted to about 3.9 with a freshly prepared solution of 2% ethanolic sulfuric acid. Evaporation of the reaction mixture to dryness yielded 4'-deoxy4-desacetylleurosidine-3-carboxhydrazide-N$^2$-succinimide sulfate.

Following the above procedure, 4-desacetyl VLB hydrazide (2.4 g) was dissolved in 125 ml of pyridine to which 385 mg of glutaric anhydride were added. N$^2$-glutaroyl 4-desacetyl-VLB-3-carboxhydrazide thus formed was isolated by the above procedure and purified by chromatography over silica gel using the same solvent system as above. The glutaroyl compound was reacted with acetic anhydride to form the mixed anhydride which cyclized spontaneously to yield 4-desacetyl-VLB-3-carboxhydrazide-N$^2$-glutarimide. The compound was purified by chromatography over silica gel using the above solvent system. A yield of 460 mg of the N$^2$-glutarimide derivative were obtained having the following physical characteristics: Mass spectrum m/e=864 (C$_{48}$H$_{60}$N$_6$O$_9$). Infrared spectrum (CHCl$_3$): peaks at 3475, 1714, and 1616 cm$^{-1}$.

pK$_a$ (66% aqueous DMF)=5.1, 7.4, 12.9.

NMR (CDCl$_3$): δ at 9.96, 8.91, 8.04, 7.52, 7.14, 6.58, 6.08, 5.83, 4.15, 3.78, 3.69, 3.61, 2.86, 0.93, 0.89.

The sulfate salt was prepared by the above procedure; yield=210 mg from 290 mg of starting material.

Following the above procedure but again substituting 4-desacetyl-VLB-3-carboxhydrazide for 4'-deoxy-4-desacetylleurosidine-3-carboxhydrazide, and using acetyl chloride in place of acetic anhydride, there was prepared N$^2$-succinoyl-4-desacetyl-VLB-3-carboxhydrazide. Chromatography of the succinimide product yielded two fractions, one of which was the expected 4-desacetyl-VLB-3-carboxhydrazide-N$^2$-succinimide and the other the 4-acetyl derivative thereof which formed as a by-product during the cyclization procedure. 4-Desacetyl-VLB-3-carboxhydrazide-N$^2$-succinimide had the following physical characteristics. Mass spectrum m/e=850 (C$_{47}$H$_{50}$N$_6$O$_9$).

Infrared spectrum (KBr): peaks at 3480, 1734 and 1616 cm$^{-1}$.

NMR (CDCl$_3$): δ at 9.69, 9.47, 8.22, 7.49, 7.12, 6.53, 6.07, 5.82, 5.71, 4.01, 3.77, 3.63, 3.59, 2.84, 2.82, and 0.89.

The sulfate salt was prepared according to the above procedure; yield=250 mg from 350 mg starting material.

The preparation of C-4 derivates of these dimeric indole-dihydroindole alkaloids variously substituted at C-3 (see R in formula I) is carried out by reacting compounds according to I where $R^1$ is H and R and $R^2$–$R^5$ have their assigned meaning in a multistep process as outlined in G.B. Patent No. 2,137,202A (previously cited), or Cullinan Ser. No. 745,562 filed 6-17-85 (Example 4). In these procedures, a cyclic anhydride of the formula

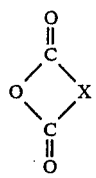

wherein X has its previous meaning, is reacted with the compound of Formula I where $R^1$ is H. The product of this reaction is a half-acid ester of the formula

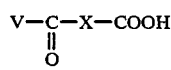

where V is the 4-desacetyl vinca alkaloid of Formula I attached through the C-4 hydroxyl. An acylating group then replaces the "OH" of the carboxylic acid (COOH). The acid chloride is a very useful acylating group. Alternatively a mixed anhydride produced by reacting, successively, N-methylmorpholine and an alkyl chloroformate with the free carboxylic acid group of the hemiacid can be used. This "activated" carboxylic acid,

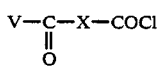

for example, is reacted with hydrazine to produce the desired hydrazide V-CO-X-CONHNH$_2$. A specific preparation illustrating this procedure follows.

Preparation II

A solution was prepared by dissolving 2.5 g of 4-desacetyl-VLB-4-hemisuccinate (4-succinoyl VLB) from Example 1 of GB patent No. 2,137,202A, in 50 ml of chloroform. 870 mg of N-methylmorpholine were added. After solution was complete, the reaction mixture was cooled in an ice bath and a stream of nitrogen introduced. 985 mg of isobutyl chloroformate were added and the reaction mixture stirred at 0° C. for about 45 minutes. One ml of anhydrous hydrazine was added and the reaction mixture stirred for about 10 minutes. The reaction mixture was then extracted with water, the water extract separated and discarded, and the organic layer dried. Evaporation of the solvent yielded a residue containing 4-desacetyl-VLB-4-hemisuccinate hydrazide. A methylene dichloride solution of the residue was chromatographed over silica gel using ethyl acetate/methanol (100/0 to 50/50) as the eluant. The appropriate fractions provided 950 mg of purified 4-desacetyl-VLB-4-hemisuccinate hydrazide; m/e=882.

The sulfate salt was prepared by dissolving the base in anhydrous ethanol (25 ml), adjusting the pH to approximately 4 with 2% ethanolic sulfuric acid, (24.5 g of anhydrous ethanol, 0.5 g of 18 M H$_2$SO$_4$) and removing the solvents in vacuo.

Infrared spectrum; peaks at 3400, 3009, 1738, 1680, and 1616 cm$^{-1}$.

NMR CDCl$_3$ δ at 9.9, 8.35, 8.05, 7.55, 7.10, 6.85, 6.10, 5.85, 5.45, 5.30, 3.80, 3.70, 3.60, 2.70, 0.90, 0.85.

The other component for our novel conjugates is an oxidized glycoprotein, preferably an immunoglobulin and, of that class, preferably a monoclonal antibody (MoAb), which is a gammaglobulin such as an IgG or an IgM. Immunoglobulin (Ig) fragments containing carbohydrate, as in the parent immunoglobulin from which these fragments are derived, can also be used to form novel conjugates of the type disclosed in this specification.

The preferred class of glycoproteins, the immunoglobulins, are those which are reactive with antigens on the surface of unwanted cells; i.e., are able to recognize antigens; have antigen recognizing properties.

Techniques for the production of such immunoglobulins from the serum of immunized animals or by culturing hybridomas secreting monoclonal products are well known. The preferred type of antibody for use in the invention is an immunoglobulin which is a gammaglobulin. IgG, IgA, IgE, and IgM subclasses are particularly preferred. Some representative immunoglobulins are as follows, mono- or polyclonal antibodies to (i) human or animal tumor associated antigens;

(ii) human B- and T-cell antigens;

(iii) human Ia antigens;

(iv) viral, fungal and bacterial antigens; and (v) cells involved in human inflammatory or allergic reactions.

Of the preferred antibodies to human or animal tumor associated antigens there may be mentioned:

(i) Ig from goats or sheep immunized with carcinoembryonic antigen;

(ii) Ig from rabbit antiacute lymphoblastic leukemia serum;

(iii) Ig from various primate antisera raised against acute lymphoblastic leukemia, acute myeloblastic leukemia, chronic lymphoblastic leukemia and chronic granulocytic leukemia;

(iv) Ig from goats or sheep immunized with lung carcinoma cells, or cellular fractions;

(v) monoclonal Ig from mouse hybridomas secreting anti-human colorectal carcinoma antibodies;

(vi) monoclonal Ig from mouse hybridomas secreting anti-human melanoma antibodies;

(vii) monoclonal Ig from mouse hybridomas that secrete antibodies reacting with human leukemia cells;

(viii) monoclonal Ig from mouse hybridomas secreting antibodies reacting with human neuroblastoma cells;

(ix) monoclonal Ig from mouse hybridomas secreting antibodies reacting with human breast cancer antigens;

(x) monoclonal Ig from mouse hybridomas secreting antibodies reacting with human ovarian carcinoma cells;

(xi) monoclonal Ig from mouse hybridomas secreting antibodies reacting with human osteosarcoma cells, with human pancreatic carcinoma cells, with human prostatic carcinoma cells etc.;

(xii) monoclonal Ig from mouse hybridomas secreting antibodies to adenocarcinomas including lung, renal, breast and pancreas;

(xiii) monoclonal Ig from mouse hybridomas secreting antibodies reacting with human squamous carcinoma cells;

(xiv) monoclonal Ig from human hybridomas (hybridomas which secrete antibodies to the human tumorassociated antigen including, but not limited to, those monoclonals above);

(xv) any antibody or fragment thereof that contains carbohydrate in either the light or heavy chain;

(xvi) Monoclonal Ig from rat, hamster, or other mammalian species not specifically mentioned above, from hybridomas which secrete antibodies to human tumor associated antigens including, but not limited to, those mentioned above.

As indicated above, the conjugate can also be made with immunoglobulin fragments Ig', referred to also as Fab, Fab', F(ab')$_2$ and IgM monomer derived from an antibody by, for example, proteolytic enzyme digestion or reductive alkylation. Such materials and methods of preparation are well known and it may be mentioned that preferred proteolytic enzymes are pepsin and papain. See generally Parham, *J. Immunology*, 131, 2895 (1983); Lamoyi et al., *J. Immunological Methods*, 56, 235 (1983); Parham, id., 53, 133 (1982); and Matthew et al., id., 50,239 (1982).

Specific MoAbs exist that are reactive against various tumors; such immunoglobulins which recognize antigens on the surface of, or otherwise associated with tumor cells, include but are not limited to the following:

TABLE I

| Tumor | MoAb | Reference |
| --- | --- | --- |
| Lung | KS1/4 | N. m. Varki, et al., Cancer Res. 44:681, 1984 |
|  | 534,F8;604A9 | F. Cuttitta, et al., in: G. L. Wright (ed) Monoclonal Antibodies and Cancer, Marcel Dekker, Inc., N.Y., p. 161, 1984. |
| Squamous Lung Cancer | G1, LuCa2, LuCa3, LuCa4 | Kyoizumi et al., Cancer Res., 45:3274, 1985 |
| Small Cell Lung Cancer | TFS-2 | Okabe et al., Cancer Res. 45:1930, 1985 |
| Colon | 11.285.14 14.95.55 | G. Rowland, et al., Cancer Immunol. Immunother., 19:1, 1985. |
|  | NS-3a-22,NS-10 NS-19-9,NS-33a NS-52a,17-1A | Z. Steplewski, et al., Cancer Res., 41:2723, 1981. |
| Melanoma | 9.2.27 | T. F. Bumol and R. A. Reisfeld, Proc. Natl. Acad. Sci., (USA), 79:1245, 1982 |
|  | p97 | K. E. Hellstrom, et al., Monoclonal Antibodies and Cancer, loc. cit. p. 31. |
|  | R24 | W. G. Dippold, et al., Proc. Natl Acad. Sci. (USA), 77 6114, 1980. |
| Neuroblastoma | P1 153/3 | R. H. Kennet and F. Gilbert, Science, 203:1120, 1979. |

TABLE I-continued

| Tumor | MoAb | Reference |
| --- | --- | --- |
|  | MIN 1 | J. T. Kemshead in Monoclonal Antibodies and Cancer, loc. cit. p. 49. |
|  | UJ13A | Goldman et al., Pediatrics, 105:252, 1984. |
| Glioma | BF7,GE2,CG12 | N. de Tribolet, et al., in Monoclonal Antibodies and Cancer, loc. cit. p. 81. |
| Breast | B6.2,B72.3 | D. Colcher, et al., in Monoclonal Antibodies and Cancer, loc. cit. p. 121. |
| Osteogenic Sarcoma | 791T/48, 791T/36 | M. J. Embleton, ibid, p. 181 |
| Leukemia | CALL 2 | C. T. Teng, et al., Lancet, 1:01, 1982. |
|  | anti-idiotype | R. A. Miller, et al., N. Eng. J. Med., 306:517, 1982. |
| Ovary | OC 125 | R. C. Bast, et al., J. Clin. Invest., 68:1331, 1981. |
| Prostate | D83.21, P6.2, Turp-27 | J. J. Starling, et al., in Monoclonal Antibodies and Cancer, loc. cit. p. 253. |
| Renal | A6H, D5D | P. H. Lange, et al., Surgery, 98:143, 1985. |

Preferred conjugates are those prepared from monoclonal antibodies, especially those which recognize human cancer cells such as adenocarcinoma, squamous cell carcinoma, transitional cell carcinoma, melanoma, neuroblastoma, small cell carcinoma, leukemia, lymphoma, and sarcoma.

A glycoprotein (GP) of the type set forth above may be oxidized by periodate or other suitable oxidizing agent so that a bond between vicinal diols in a surface carbohydrate is ruptured and aldehyde groups on either side of the original bond are produced thereby.

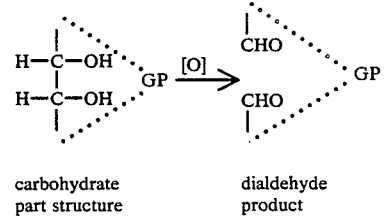

carbohydrate part structure     dialdehyde product

The number of dialdehyde units produced is a result of the following factors as will be appreciated by those skilled in the art: amount of periodate employed, general reaction conditions of oxidation (e.g., time, temperature, solvent, concentration, etc.), number of vicinal diol carbohydrate units present on the protein, and their accessibility to the periodate reagent.

Alternatively, or in combination with the periodate oxidation above, one may employ enzymatic oxidation with galactose oxidase. This is a more selective and restrictive reagent catalyzing the conversion of the 6—CH$_2$OH position of galactose residues on the glycoprotein carbohydrate chains to an aldehyde functionality. This 6—$CH_2OH$ group must be unsubstituted to allow for successful oxidation, and unmasking a blocked group, such as a group wherein a sialic acid residue is attached, may be accomplished with the enzyme neuraminidase. As above, the number of aldehyde moieties so produced will be a function of many variables.

The aldehyde-containing glycoproteins, $(OCH)_m$-GP, are then conjugated with the vinca hydrazide, V'-3-$CONHNH_2$ or V-CO-X-$CONHNH_2$, to produce a hydrazone, (V'-3-CONHN=CH)$_m$-GP or (V-COX-CONHN=CH)$_m$-GP, where V' is the vinca radical defined in Formula I, less the -COR radical at the 3-position, and m is the number of aldehyde or vinca groups attached to the glycoprotein. These conjugates are the subject of this invention.

In general, the number represented by m is a function of the number of aldehyde groups arising from the oxidation procedures described above. We have found conjugates with average ratios (vinca residues per antibody) of about 1–10 (i.e., m is 1–10), with ratios of about 4–10 preferred.

The conjugation of the vinca hydrazides with oxidized glycoproteins is accomplished by standard methods known in the art. In general, a solution of the vinca in a water-miscible solvent such as dimethylformamide is added to a chilled buffered aqueous solution of the oxidized glycoprotein. Temperatures of about 0°–8° C. are preferred and a 0.1N sodium acetate buffer is normally employed. The reaction is best carried out in the dark and under an inert atmosphere. The reaction is usually complete in about 10–24 hours and the resulting conjugate may be purified by standard methods, such as by chromatography over Sephadex.

The oxidation and conjugation of specific MoAbs follows.

Preparation III

Conjugates with X-63AG8-S1 MoAb.

A solution was prepared by dissolving 200 mg of X-63AG8-S1 (mw=approximately 150,000, $1.34 \times 10^{-6}$ moles) in 20 ml of a 0.1M sodium acetate buffer pH 5.6 (29.3 g sodium acetate, 2.44 ml acetic acid plus sufficient sterilized water to make 4L of buffer). The solution was stored at about 0° C. overnight (about 10% of the protein had not dissolved). 685 mg of sodium metaperiodate were added in a single batch with rapid stirring.

The mixture was stirred for 21 minutes at about 0° C. in the dark and was then quenched by the addition of a 5-fold excess (for the total periodate) with 1.28 ml of a 12.5M solution of ethylene glycol in sterile water. The new mixture was stirred at 0° C. for 5 minutes in the dark and was then centrifuged to leave a clear supernatant and a white pellet. The supernatant was loaded onto a Sephadex G25 (medium mesh) gel column and the product eluted with the same sodium acetate buffer. The eluate was monitored with UV light at 280 nm. Any periodate was washed from the column and discarded. Concentration of the oxidized product was assessed in each eluate fraction at 279 nm; yield was 96%. A second run carried out identically gave a 96.5% yield.

The above eluate solutions containing 4.72 and 4.02 mg/ml of oxidized product were mixed and 0.1N sodium acetate buffer added to give a final protein concentration of 2.77 mg/ml (Total volume=69 ml). The solution was cooled to about 0° C.

A solution of 4-desacetyl VLB 3-carboxhydrazide in DMF (5.6 ml of a 53.7 mg/ml solution) was added in dropwise fashion to the chilled buffered MoAb solution. The reaction vessel was flushed with nitrogen gas and then sealed. The reaction mixture was stirred in the cold and dark with magnetic stirring for 24 hours. The reaction vessel was then unsealed and the clear, pale yellow reaction mixture was centrifuged. The supernatant was chromatographed over Sephadex G25 gel preequilibrated with pH=7.4 phosphate buffered saline (0.01M $H_3PO_4$, 0.15M NaCl) which was also used as the eluant. The conjugate (formed by hydrazone formation between the 3-carboxhydrazide group and an aldehyde group in a carbohydrate on the MoAB) was eluted first followed by unreacted 4-desacetyl VLB 3-carboxhydrazide. The yield of conjugate obtained (from 4 columns) was 173 mg in 224 ml (90% yield). The conjugate contained about 6 moles of 4-desacetyl-VLB-3-carboxhydrazone per mole of X-63AG8-S1 MoAb.

A second complete run was carried out using 200 mg of KS1/4 (a MoAb capable of recognizing surface antigens of human adenocarcinoma cells) in 20.0 ml of acetate buffer and using the same quantities of periodate and ethylene glycol as in Preparation 3. The run gave 176 mg of oxidized MoAb in 39.9 ml of buffer after chromatography (88% yield). Conjugation with 274 mg of 4-desacetyl-VLB-3-carboxhydrazide in pH=5.6 acetate buffer gave 146 mg (83% yield) of conjugate containing about 7.5 moles of 4-desacetyl-VLB-3-carboxhydrazone per mole of KS1/4.

Following the above procedure, a conjugate was prepared by reacting 4-desacetyl-VLB-3-carboxhydrazide with aldehyde groups formed by oxidation of the surface carbohydrates of 9.2.27, a glycoprotein MoAb capable of recognizing antigenic sites on the surface of human melanoma cells. A run using 200 mg of the MoAb oxidized with 685 mg of sodium metaperiodate in pH=5.6 acetate buffer (0.1 molar) gave an aldehyde-containing oxidized 9.2.27 MoAb in 92% yield (184 mg). This material was conjugated with 4-desacetyl-VLB-3-carboxhydrazide (279 mg). Final yield of the poly 4-desacetyl-VLB-hydrazone of oxidized, aldehyde group-containing 9.2.27 conjugate was 91% as a solution in phosphate buffered saline.

As indicated above, conjugates can also be made with immunoglobulin fragments Ig', IgM monomer, or other Ig monomers, containing carbohydrate derived from a parent antibody by, for example, proteolytic enzyme digestion or reductive alkylation. Such materials and methods of preparation are well known and it may be mentioned that preferred proteolytic enzymes are pepsin and papain.

Evaluation of the conjugates of this invention can be carried out using well known techniques such as affinity chromatography. The efficacy of the conjugate can be estimated by counting the number of viable cells after treatment of a suspension of tumor cells with the conjugate, or from measurements of the uptake of tritiated uridine. Protein and drug concentrations are determined by measuring optical densities of conjugate solutions at two wavelengths, for example 270 and 279 nm, and relating the values obtained to those for the free drug and unconjugated immunoglobulin at the same two wavelengths. The conjugate can also be evaluated in vivo against human tumor xenografts in athymic mice.

The novel conjugates of the invention are useful in the treatment of cancers and as such are preferably prepared for use in formulations suitable for injection. Thus the invention includes a pharmaceutical formulation, for example an injectable preparation comprising a conjugate of the invention together with a pharmaceutically-acceptable carrier or diluent such as are well known in the art. The formulation is preferably in unit dosage form, each dosage containing, for example, from 0.01 to 10 mg of the active ingredient (in terms of the vinca drug moiety).

The novel conjugates are effective over a wide dosage range and dosages per week, for example, for the treatment of adult humans suffering from cancer will normally fall within the range of 0.01 to 10 mg/kg (vinca drug moiety), more usually in the range of from 0.03 to 9 mg/kg. However it will be understood that the amount of conjugate actually administered will be determined by a physician in the light of the relevant circumstances, including the condition to be treated and the chosen route of administration.

We claim:

1. A cytotoxic hydrazone conjugate formed by reacting a vinca hydrazide of the formula

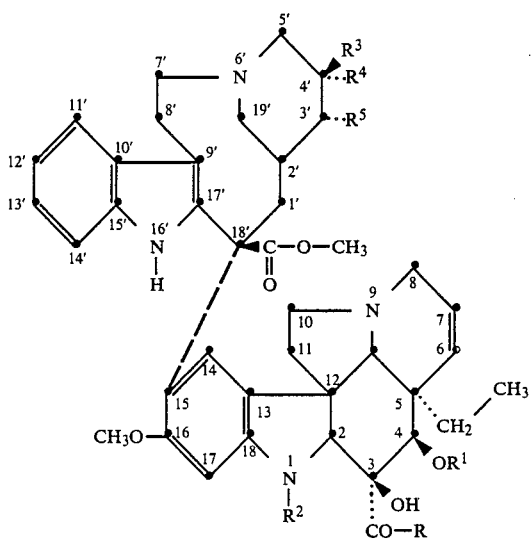

I wherein $R^2$ is H, $CH_3$ or CHO; when $R^4$ and $R^5$ are taken singly, $R^5$ is H, and one of $R^3$ and $R^4$ is ethyl and the other is H or OH; when $R^4$ and $R^5$ are taken together with the carbons to which they are attached, they form an oxirane ring in which case $R^3$ is ethyl; R is $NHNH_2$,

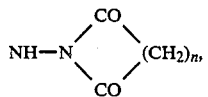

$O(C_{1-3}$ alkyl), $NH_2$, $NH(C_{1-3}$ alkyl), $NH\text{-}CH_2CH_2\text{-}Y$, 1-pyrrolidinyl or 1-piperidinyl, wherein n is 2–4 and Y is Cl, $OCH_3$ or $SCH_3$; $R^1$ is H, $(C_{1-3}$ alkyl)-CO, chlorosubstituted $(C_{1-3}$ alkyl)-CO or $R^6$ wherein $R^6$ is COX-$CONHNH_2$ wherein X is $C_{1-4}$ straight chain alkylene, $C_{2-8}$ branched chain alkylene, $C_{2-4}$ alkenylene, $C_{3-4}$ alkynylene, $C_{3-6}$ cycloalkylene, phenylene, hydroxy-substituted $C_{1-4}$ alkylene, or a direct bond, provided that either R is $NHNH_2$ or $R^1$ is $R^6$ except that R cannot be $NHNH_2$ when $R^1$ is $R^6$ and $R^1$ cannot be $R^6$ when R is $NHNH_2$, with one or more aldehyde groups of an oxidized glycopotein.

2. A conjugate according to claim 1 wherein the vinca hydrazide is 4-desacetyl-VLB-3-carboxhydrazide.

3. A conjugate according to claim 1 wherein the vinca hydrazide is 4-desacetyl-VLB-4-hemisuccinate hydrazide.

4. A conjugate according to claim 1 wherein the vinca hydrazide is 4-desacetyl-VLB-3-carboxhydrazide-$N^2$-succinimide-4-hemisuccinate hydrazide.

5. A conjugate according to claim 1 wherein the vinca hydrazide is 4-desacetyl-VLB-3-carboxamide-4-hemisuccinate hydrazide.

6. A conjugate according to claim 1 wherein the vinca hydrazide is 4-desacetyl-VLB-4-hemiglutarate hydrazide.

7. A conjugate according to claim 1 wherein the vinca hydrazide is 4-desacetyl-VCR-4-hemisuccinate hydrazide.

8. A conjugate according to claim 1 wherein the vinca hydrazide is 4-desacetyl-4'-epideoxy-VLB-4-hemisuccinate hydrazide.

9. A conjugate according to claim 1 wherein the vinca hydrazide is 4-desacetyl-VLB-3-carboxhydrazide-$N^2$-glutarimide-4-hemisuccinate hydrazide.

10. A conjugate according to claim 1 wherein the vinca hydrazide is 4-desacetyl-VCR-3-carboxhydrazide.

11. A conjugate according to claim 1 wherein the vinca hydrazide is 4-desacetyl-4'-epideoxy-VLB-3-carboxhydrazide.

12. A conjugate according to claim 1 in which the oxidized glycoprotein is derived from an immunoglobulin having antigen recognizing properties.

13. A conjugate according to claim 12 in which the immunoglobulin is a monoclonal antibody.

14. A conjugate according to claim 13 in which the MoAb is adapted for recognition of antigens on the surface of unwanted mammalian cells.

15. A conjugate according to claim 13 in which the MoAb is adapted for recognition of human cancer cells selected from the group consisting of adenocarcinoma, squamous cell carcinoma, transitional cell carcinoma, melanoma, neuroblastoma, small cell carcinoma, leukemia, lymphoma, and sarcoma.

16. A conjugate according to claim 13 wherein the vinca hydrazide is 4-desacetyl-VLB-3-carboxhydrazide.

17. A conjugate according to claim 13 wherein the vinca hydrazide is 4-desacetyl-VLB-4-hemisuccinate hydrazide.

18. A conjugate according to claim 13 wherein the vinca hydrazide is 4-desacetyl-VLB-3-carboxhydrazide-$N^2$-succinimide-4-hemisuccinate hydrazide.

19. A conjugate according to claim 16 wherein the MoAb is adapted for recognition of human adenocarcinoma cells.

20. A conjugate according to claim 17 wherein the MoAb is adapted for recognition of human adenocarcinoma cells.

* * * * *